(12) United States Patent
Perkins (10) Patent No.: US 8,285,564 B2
(45) Date of Patent: Oct. 9, 2012

(54) WIRELESS TRACKING SYSTEM AND METHOD FOR ANALYZING AN INTERACTION BETWEEN OBJECTS

(75) Inventor: Matthew R. Perkins, San Diego, CA (US)

(73) Assignee: Awarepoint Corporation, San Diego, CA (US)

( * ) Notice: Subject to any disclaimer, the term of this patent is extended or adjusted under 35 U.S.C. 154(b) by 349 days.

(21) Appl. No.: 12/484,236

(22) Filed: Jun. 14, 2009

(65) Prior Publication Data

US 2010/0256983 A1    Oct. 7, 2010

Related U.S. Application Data

(60) Provisional application No. 61/166,755, filed on Apr. 5, 2009.

(51) Int. Cl.
   *G06Q 10/00* (2006.01)
(52) U.S. Cl. .................................. 705/3; 705/2
(58) Field of Classification Search ................... 705/2, 3
   See application file for complete search history.

(56) References Cited

U.S. PATENT DOCUMENTS

| | | |
|---|---|---|
| 3,805,265 A | 4/1974 | Lester |
| 5,732,401 A | 3/1998 | Conway |
| 5,977,913 A | 11/1999 | Christ |
| 6,915,135 B1 | 7/2005 | McKee et al. |
| 7,050,819 B2 | 5/2006 | Schwengler |
| 7,053,831 B2 | 5/2006 | Dempsey et al. |
| 7,099,895 B2 | 8/2006 | Dempsey |
| 7,312,752 B2 | 12/2007 | Smith et al. |
| 7,324,824 B2 | 1/2008 | Smith et al. |
| 7,336,182 B1 * | 2/2008 | Baranowski et al. ...... 340/572.1 |
| 7,382,247 B2 | 6/2008 | Welch et al. |
| 7,403,111 B2 | 7/2008 | Tessier et al. |
| 2004/0147232 A1 | 7/2004 | Zodnik |
| 2005/0250552 A1 | 11/2005 | Eagle et al. |
| 2007/0208598 A1 * | 9/2007 | McGrady et al. ................. 705/3 |
| 2008/0012767 A1 | 1/2008 | Caliri et al. |
| 2008/0133127 A1 | 6/2008 | Havens |
| 2008/0147529 A1 * | 6/2008 | Kreiner et al. ................... 705/34 |
| 2009/0204434 A1 * | 8/2009 | Breazeale, Jr. ................... 705/3 |

OTHER PUBLICATIONS

International Search Report and Written Opinion for PCT/US2010/028977 a related PCT application.

* cited by examiner

*Primary Examiner* — Robert Morgan
*Assistant Examiner* — Maroun Kanaan
(74) *Attorney, Agent, or Firm* — Clause Eight IPS; Michael Catania (57) ABSTRACT

The present invention provides a solution to determining an interaction between objects through wireless tracking. The present invention utilizes communication devices attached to objects that transmit signals for reception by sensors stationed throughout a facility which forward the signals to an information engine for analysis.

18 Claims, 8 Drawing Sheets

WIRELESS TRACKING SYSTEM AND METHOD FOR ANALYZING AN INTERACTION BETWEEN OBJECTS

CROSS REFERENCES TO RELATED APPLICATIONS

The Present Application claims priority to U.S. Provisional Patent Application No. 61/166,755, filed on Apr. 5, 2009.

STATEMENT REGARDING FEDERALLY SPONSORED RESEARCH OR DEVELOPMENT

Not Applicable

BACKGROUND OF THE INVENTION

1. Field of the Invention

The present invention is related to wireless tracking systems and methods. More specifically, the present invention relates to a system and method for analyzing an interaction between objects such as people.

2. Description of the Related Art

Real-time knowledge of resources, whether the resources are assets or people, is becoming a necessary tool of many businesses. Real-time knowledge of the location, status and movement of crucial resources can allow a business to operate more efficiently and with fewer errors. However, many businesses employ hundreds if not thousands of resources in a single facility, and these resources need to be accounted for by a central system that is user friendly.

For example, in a typical hospital there are numerous shifts of employees that utilize the same equipment. When a new shift arrives, the ability to quickly locate medical equipment not only results in a more efficient use of resources, but also can result in averting a medical emergency. Thus, the tracking of medical equipment in a hospital is becoming a standard practice.

The tracking of objects in other facilities is rapidly becoming a means of achieving greater efficiency. A typical radio frequency identification system includes at least multiple tagged objects, each of which transmits a signal, multiple receivers for receiving the transmissions from the tagged objects, and a processing means for analyzing the transmissions to determine the locations of the tagged objects within a predetermined environment.

Several prior art references discloses various tracking systems.

McKee et al., U.S. Pat. No. 6,915,135 discloses a system for determining presence, identity and duration of presence in a given area (a table in a restaurant) of an object (tag attached to a waiter).

Lester, U.S. Pat. No. 3,805,265 discloses a location system that uses line-of-sight radiant wave energy for signal transmission.

Schwengler U.S. Pat. No. 7,050,819, is directed at the problem of adequate power for a mobile telephone for a two-way communication function or a regeneration function as a node of a mesh network.

Christ, U.S. Pat. No. 5,977,913, discloses a radiofrequency system that is utilized within a prison and allows for an individual to be located after an alarm is triggered by the individual.

Zodnik, U.S. Patent Publication Number 2004/0147232, discloses wall-mounted (RJ-11 or RJ-45) wireless transceivers configured to only track the location of a self-identified wireless communication device in order to communicate the location of the self-identified wireless communication device to an emergency service such as 911.

Welch et al., U.S. Pat. No. 7,382,247 for a Personal Status Physiologic Monitor System And Architecture And Related Monitoring Methods, discloses a systems for monitoring a patient that uses a personal status monitoring device, such as a ECG electrode assembly, which transmits a signal to an intermediary device, such as a PDA, which transmits to a server using a WLAN.

Tessier et al., U.S. Pat. No. 7,403,111 for a Location System Using A First Signal To Gate A Second Signal, discloses an object identifier that transmits both an IR signal and a RF signal for location determination.

Dempsey et al., U.S. Pat. No. 7,053,831 for a Location System, discloses a system which allows for a location to be determined without requiring precise calculations through use of an object identifier that transmits one identifier corresponding to an object identifier and a second identifier which is a group identifier.

Dempsey, U.S. Pat. No. 7,099,895 for a System And Method For Performing Object Association Using A Location Tracking System, discloses a system for recording object associations based on signals for object identifiers.

Eagle et al., U.S. Patent Publication Number 2005/0250552, for a Combined Short Range Radio Network And Cellular Telephone Network For Interpersonal Communications, discloses a system that uses BLUETOOTH technology integrated in a cellular telephone to provide interpersonal communications between individuals.

As stated above, the problem is inadequate resource visibility in a business. Businesses such as hospitals, need to locate resources (assets and people), know the status of the resources, and understand the usage history of the resources to enable business improvement.

Specific problems for hospitals include tracking infections in a hospital to determine a source and other areas or individuals that may be infected. Other problems include spotting emerging patterns of infection and outbreaks to mitigate those affected. Further, for MEDICARE and other insurance providers, hospitals and other medical facilities need to demonstrate that patients received their required care in order to receive payment for such care. The prior art has failed to provide an adequate solution to these problems.

BRIEF SUMMARY OF THE INVENTION

The present invention provides a solution to determining an interaction between objects through wireless tracking. The present invention utilizes communication devices attached to objects that transmit signals for reception by sensors stationed throughout a facility which forward the signals to an information engine for analysis.

One aspect of the present invention is a system for determining a business relationship between individuals within a facility. The system includes multiple first tags, multiple second tags, a mesh network and an information engine. The mesh network is preferably a 802.15.4 ZIGBEE wireless sensor network. Each of the first tags represents a first object. Each of the second tags represents a second object. The mesh network includes multiple plug-in sensors located within the facility. The information engine is in communication with the mesh network. The information engine determines a business relationship between a first object and a second object having an interaction based on at least two of multiple factors which include a position location of the interaction, a duration of the interaction, a previous location of the first object, a previous location of the second object and the number of other objects located near the interaction.

In a preferred embodiment, the first object is a first person and the second object is a second person and the plurality of factors further includes a position designation of the first person and a position designation of the second person and a number of previous interactions between the first person and the second person within a predetermined time period. Alternatively, the first object is fixed or mobile and the second object is mobile. Alternatively, the first object is a group of objects and the second object is a group of objects. Alternatively, the first object is fixed and the second object is a group of objects. Alternatively, the first object is mobile and the second object is a group of objects. Alternatively, the first object is a group of mobile objects and the second object is a group of mobile objects. Each of the first tags can be mounted on a corresponding identification card, or can be an identification card.

Another aspect of the present invention is a method for determining a business relationship between individuals within a facility. The method includes transmitting a signal from a first tag associated with a first person. The method also includes transmitting a signal from a second tag associated with a second person. The method also includes receiving the signal from the first tag and the signal from the second tag at a mesh network established within the facility. The method also includes determining that an interaction is occurring between the first person and the second person. The method also includes determining a business relationship between the first person and the second person based on multiple factors. The multiple factors can include a position location of the interaction, a duration of the interaction, a previous location of the first person prior to the interaction, a previous location of the second person prior to the interaction, a position designation of the first person and a position designation of the second person, a number of previous interactions between the first person and the second person within a predetermined time period, and the number of other persons at the interaction.

Yet another aspect of the present invention is a system for determining a business relationship between individuals within a facility. The system includes multiple peer-to-peer communication devices, multiple tags, a mesh network and an information engine. Each of the peer-to-peer communication devices is associated with an individual person. Each of the tags represents a first object. The mesh network includes multiple plug-in sensors located within the facility. The information engine is in communication with the mesh network. The information engine analyzes an interaction between a first object and a second object based on multiple factors. The multiple factors include a position location of the interaction, a duration of the interaction, a previous location of the first person prior to the interaction, and information for a mobile object within a predetermined distance of the location of the interaction.

In one example, the information engine analyzes the interaction to determine a billing charge for services of the first person. In another example, the facility is a hospital and the information engine analyzes the interaction to determine medical services provided to a patient.

Yet another aspect of the present invention is a system for analyzing an action of an individual. The system includes tracking devices, tags, a mesh network and an information engine. Each of the tracking devices is associated with an individual person. Each of the tags is associated with a mobile object. The mesh network includes multiple sensors positioned within a facility. The mesh network receives transmissions from each tags and each of the tracking devices. The information engine is in communication with the mesh network. The information engine analyzes an action of a first person based on a plurality of factors including a position location of the action, a duration of the action, a previous location of the first person prior to the action, and information for a mobile object within a predetermined distance of the location of the action.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
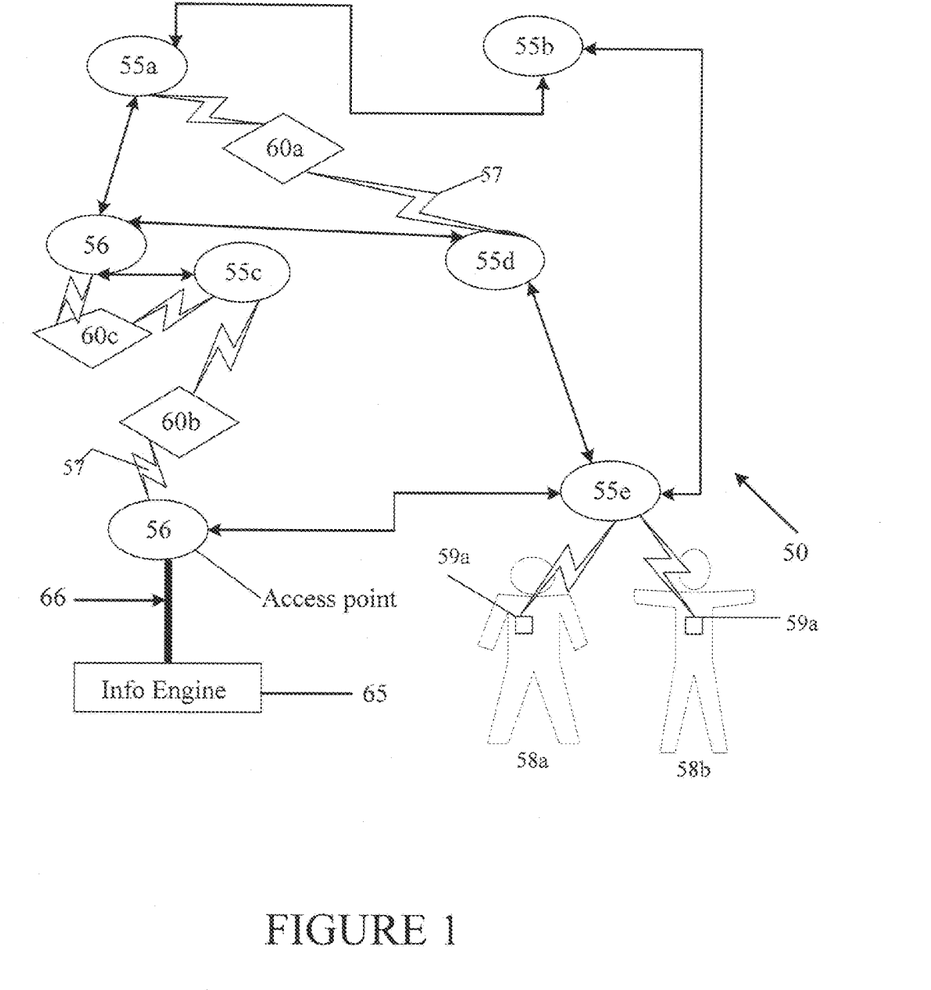
FIG. 1 is schematic view of a system for analyzing an interaction between objects.
Figure 2:
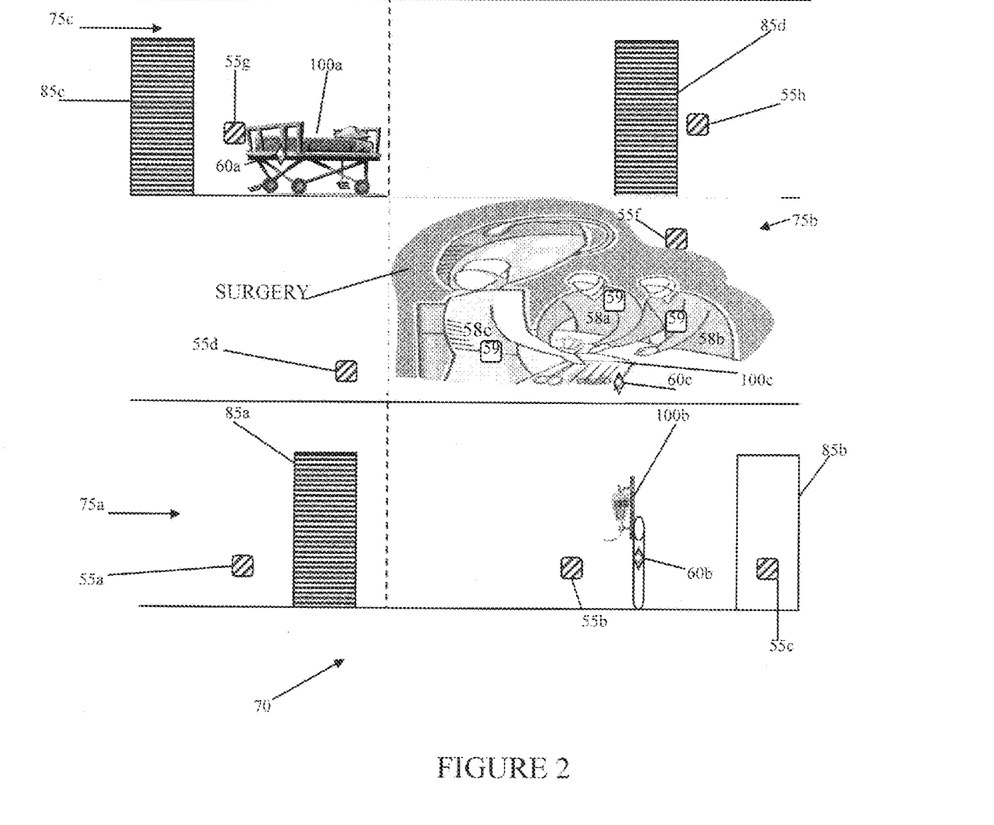
FIG. 2 is a multi-floor view of a facility employing a system for analyzing an interaction between objects.
Figure 3:
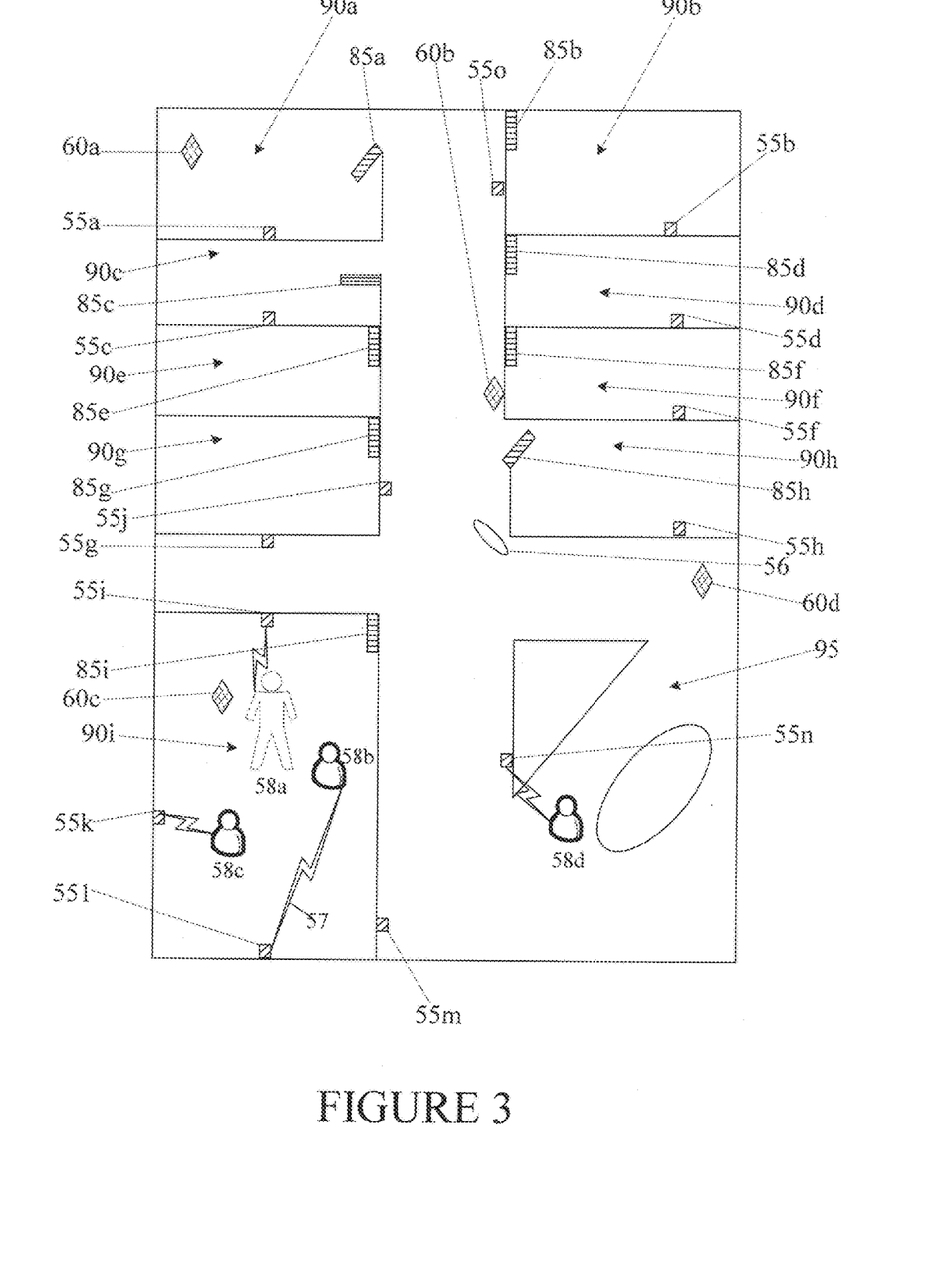
FIG. 3 is a floor plan view of a single floor in a facility employing the system for analyzing an interaction between objects.

As shown in FIGS. 1-3, a system for tracking objects within a facility is generally designated 50. The system 50 is capable of analyzing an interaction between objects, individuals 58 and/or devices 100. The system 50 preferably includes a plurality of sensors 55, a plurality of bridges 56, a plurality of communication devices 59, a plurality of tags 60, and at least one information engine 65. The sensors 55 form a mesh network for receiving signals from the communication devices 59 and tags 60. One example of the components of the system 50 is disclosed in U.S. Pat. No. 7,197,326, for a Wireless Position Location And Tracking System, which is hereby incorporated by reference in its entirety. A more specific example of the sensors 55 is disclosed in U.S. Pat. No. 7,324,824, for a Plug-In Network Appliance, which is hereby incorporated by reference in its entirety.

The system 50 is preferably employed at a facility 70 such as a business office, factory, home, hospital and/or government agency building. The system 50 is preferably utilized to track and locate various objects positioned throughout the facility 70 in order to analyze interactions between objects. The communication devices 59 and tags 60 preferably continuously transmit signals on a predetermined time cycle, and these signals are received by sensors 55 positioned throughout the facility 70. Alternatively, the tags 60 and communication devices 59 transmit signals in a random, ad-hoc or dynamic manner, and these signals are received by the sensors 55 positioned throughout the facility 70. The sensors 55 transmit the data from the communication devices 59 and tags 60 to a bridge 56 for transmission to the information engine 65. If a sensor 55 is unable to transmit to a bridge 56, the sensor 55 may transmit to another sensor 55 in a mesh network for eventual transmission to a bridge 56. In a preferred embodiment, a transmission may be sent from a transmission distance of six sensors 55 from a bridge 56. Alternatively, a transmission is sent from a transmission distance ranging from ten to twenty sensors 55 from a bridge 56. The information engine 65 preferably continuously receives transmissions from the mesh network formed by the sensors 55 via the bridges 56 concerning the movement of persons 58 bearing a communication device 59 and/or devices 100 bearing a tag 60 within the facility 70. The information engine 65 processes the transmissions from the sensors 55 and calculates a real-time position for each of the objects, persons 58 bearing a communication device 59 or devices 100 bearing a tag 60, within the facility 70. The real-time location information for each of the objects is preferably displayed on an image of a floor plan of the facility 70, or if the facility 70 has multiple floors, then on the floor plan images of the floors of the facility 70. The floor plan image may be used with a graphical user interface of a computer, personal digital assistant, or the like so that an individual of the facility 70 is able to quickly locate objects 100 within the facility 70.

As shown in FIG. 1, the system 50 utilizes sensors 55 to monitor and identify the real-time position of non-stationary objects bearing or integrated with communication devices 59. The sensors 55a-f preferably wirelessly communicate with each other (shown as double arrow lines) and with an information engine 65 through a wired connection 66 via at least one bridge 56, such as disclosed in the above-mentioned U.S. Pat. No. 7,324,824 for a Plug-In Network Appliance. The communication devices 59 and tags 60 transmit wireless signals 57 which are received by the sensors 55a-e, which then transmit signals to bridges 56 for eventual transmission to the information engine 65. The information engine 65 is preferably located on-site at the facility 70. However, the system 50 may also include an off-site information engine 65, not shown.

In a preferred embodiment, each communication device 59 and tag 60 preferably transmits a radio frequency signal of approximately 2.48 GigaHertz ("GHz"). The communication format is preferably IEEE Standard 802.15.4. Alternatively, each communication device 59 and tag 60 transmits an infrared signal or an ultrasound signal. The transmission range is preferably between 1 and 3 meters. The tags 60 may be constructed with an asset theft protection system such as disclosed in Baranowski et al., U.S. Pat. No. 7,443,297 for a Wireless Tracking System And Method With Optical Tag Removal Detection, which is hereby incorporated by reference in its entirety. The tags 60 and communication devices 59 may be designed to avoid multipath errors such as disclosed in Nierenberg et al., U.S. Pat. No. 7,504,928 for a Wireless Tracking System And Method Utilizing Tags With Variable Power Level Transmissions, and Caliri et al., U.S. Patent Publication Number 2008/0012767 for a Wireless Tracking System And Method With Multipath Error Mitigation, both of which are hereby incorporated by reference in their entireties.

As shown in FIGS. 2-3, the facility 70 is depicted as a hospital. The facility 70 has multiple floors 75a-c. Each floor 75a, 75b and 75c has multiple rooms 90a-i, with each room 90 accessible through a door 85. Positioned throughout the facility 70 are sensors 55a-o for obtaining readings from communication devices 59 and tags 60 attached to people or devices. A bridge 56 is also shown for receiving transmissions from the sensors 55 for forwarding to the information engine 65. For example, as shown in FIG. 2, the system 50 determines that individuals 58a, 58b and 58c are located in a surgery room and are using device 100c, which is a surgical kit. The information engine 65 analyzes the interaction by monitoring the duration of the interaction, the devices 100 utilized, the location of the interaction (surgery), the previous location of the individuals 58 (possibly a surgical prep room) and additional factors. In another example, as shown in FIG. 3, the system 50 determines that individuals 58a, 58b and 58c are located in a patient's room and are using device with an attached tag 60c, which is a patient monitoring device. In this example, individual 58a is a patient, individual 58b is a physician, and individual 58c is a nurse. The information engine 65 analyzes the interaction by monitoring the duration of the interaction, the devices 100 utilized, the location of the interaction (patient's room), the previous location of the individuals 58 and additional factors. The information engine 65 uses this data to generate billing information for the patient.

Figure 4:
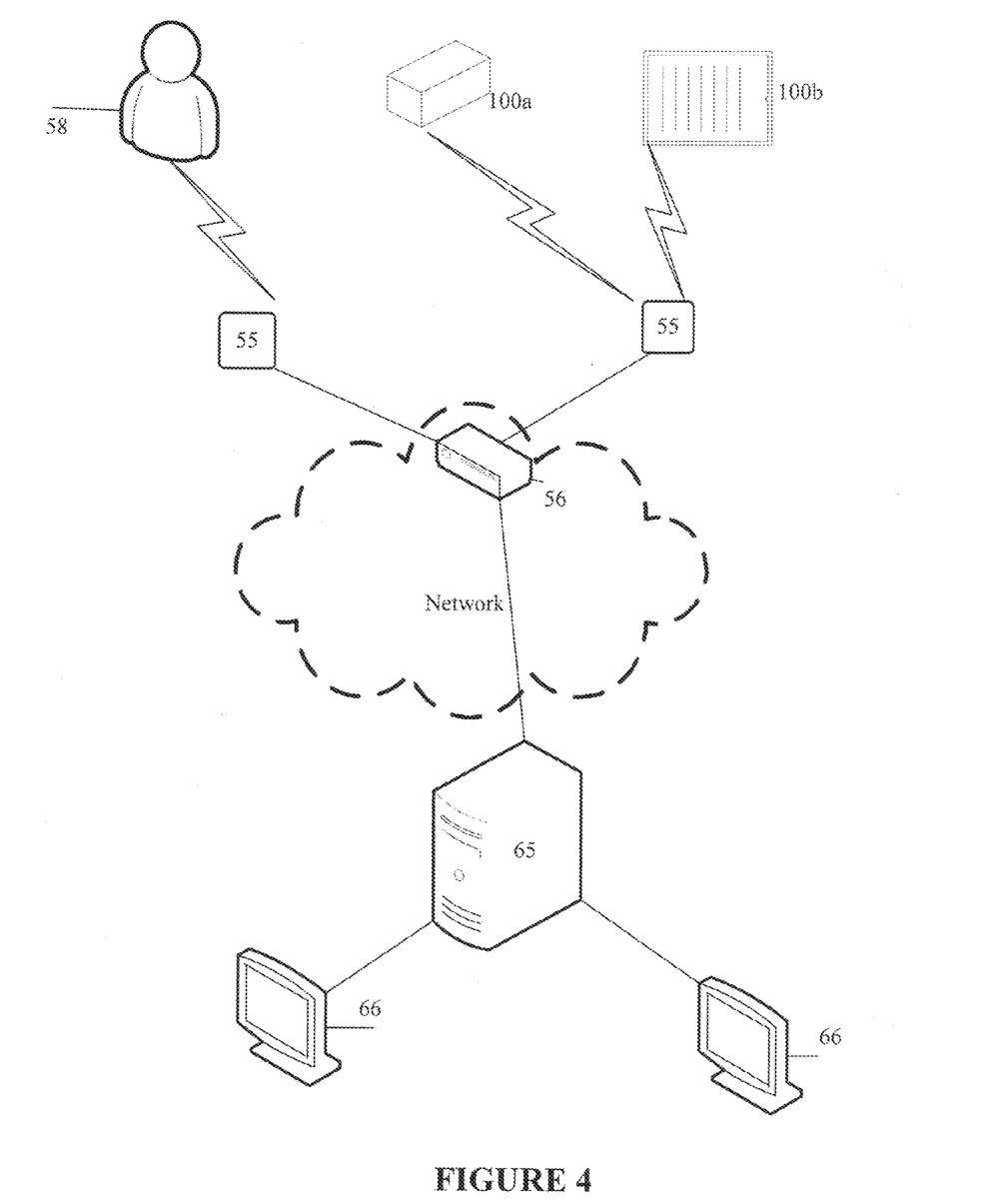
FIG. 4 is a block diagram of a flow of information utilizing a system for analyzing an interaction between objects.

FIG. 4 illustrates a preferred architecture of the system 50. For description purposes, the information providers are set forth on one side of the network and the operations is set forth on the other side of the network. However, those skilled in the pertinent art will recognize that the illustrated architecture of the system 50 is not meant to limit any physical relationship between information providers and operations. In fact, an individual 58 could be tracked while accessing information from a device 100 such as a computer 66 in operations. The information providers include individuals 58 that wear communication devices 59, equipment 100a bearing tags 60, sterilizable equipment 100b bearing sterilizable tags 60, and the like. A description of sterilizable tags 60 is found in Caliri et al., U.S. patent application Ser. No. 12/325,030 for Wireless Tracking System And Method With Extreme Temperature Resistant Tag, which is hereby incorporated by reference in its entirety. A bridge 56 acts as an intermediary between the information providers and operations. The bridge 56 communicates information to the information engine 65 which analyzes the information to determine an interaction between objects for access through an enterprise local area network for display on computers 66 or other graphical user interface devices.

Figure 5:
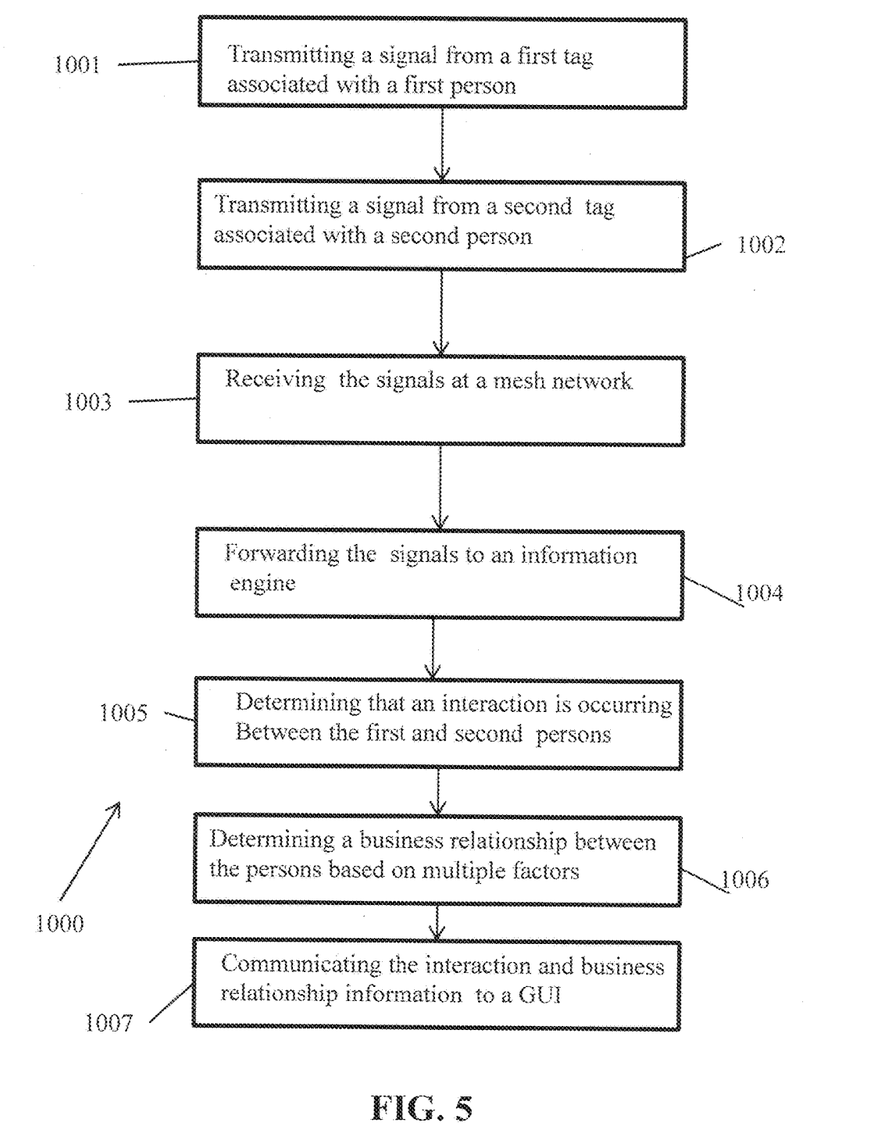
FIG. 5 is a flow chart of a method for analyzing an interaction between objects.

A method 1000 for analyzing an interaction between objects within a facility is illustrated in FIG. 5. At block 1001, a first wireless signal is transmitted from a communication device associated with an object, in this case a first person. At block 1002, a second wireless signal is transmitted from a communication device associated with the object, in this case a second person. At block 1003, the first and second wireless signals are received at least one of a plurality of sensors positioned within a facility. At block 1004, the signals are forwarded to an information engine. At block 1005, the information engine determines that an interaction is occurring between the persons. At block 1006, the information engine determines a business relationship between the persons based on multiple factors. As used herein, a business relationship involves more than just a commercial transaction between individuals, and could be an interaction between colleagues, an interactions between patients in a hospital, an interactions between employers during non-business hours, and the like. The multiple factors include a position location of the interaction, a duration of the interaction, a previous location of the first person prior to the interaction, and information for a mobile object within a predetermined distance of the location of the interaction. At block 1007, the interaction and business relationship information is communicated to a graphical user interface.

Figure 6:
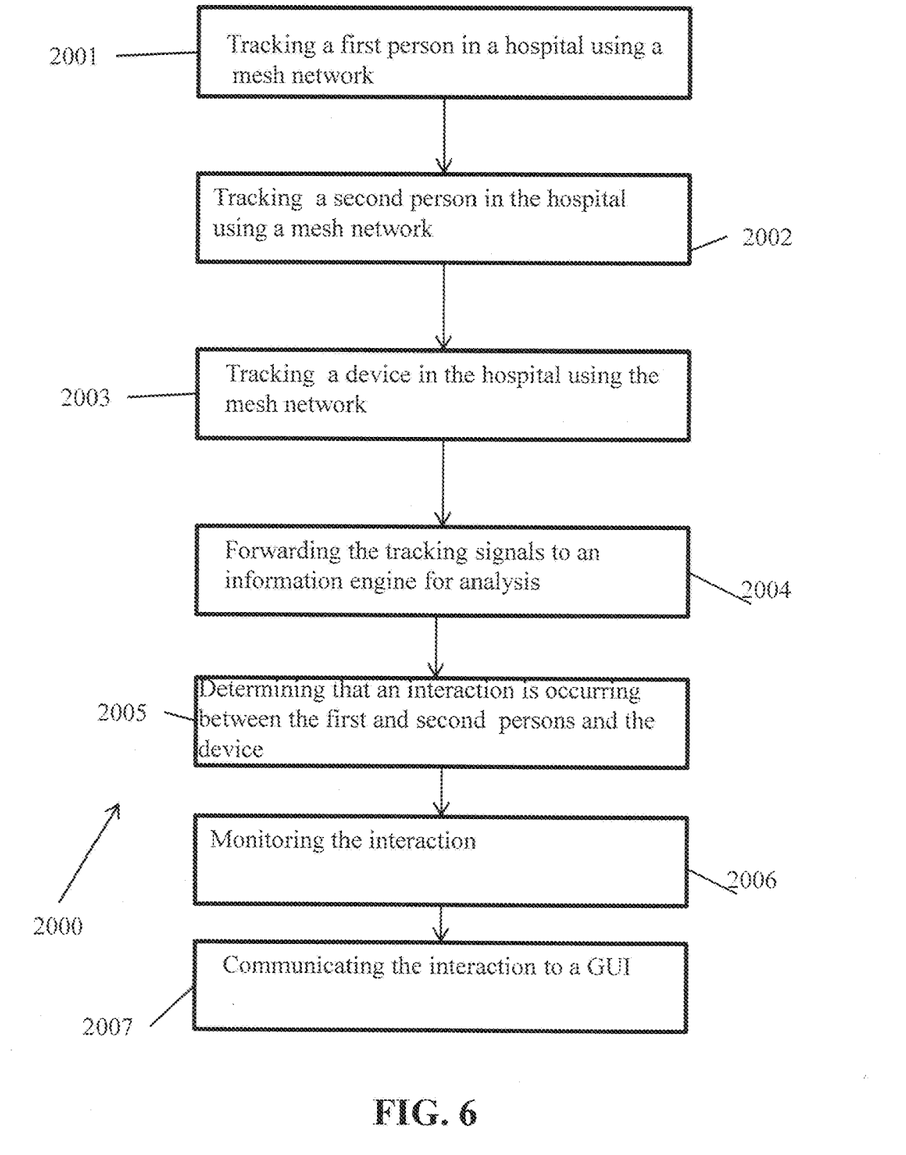
FIG. 6 is a flow chart of a method for analyzing an interaction between objects.

Another method 2000 for analyzing an interaction between objects within a facility is illustrated in FIG. 6. At block 2001, a first person is tracked within a hospital using a mesh network that receives signals intermittingly transmitted from a communication device 59 associated with the first person. At block 2002, a second person is tracked within a hospital using a mesh network that receives signals intermittingly transmitted from a communication device 59 associated with the second person. At block 2003, a device is tracked within a hospital using a mesh network that receives signals intermittingly transmitted from a tag 60 associated with the device. At block 2004, the signals are forwarded to an information engine. At block 2005, the information engine determines that an interaction is occurring between the persons and device. At block 2006, the information engine through the mesh network monitors the interaction. At block 2007, the interaction information is communicated to a graphical user interface.

Figure 7:
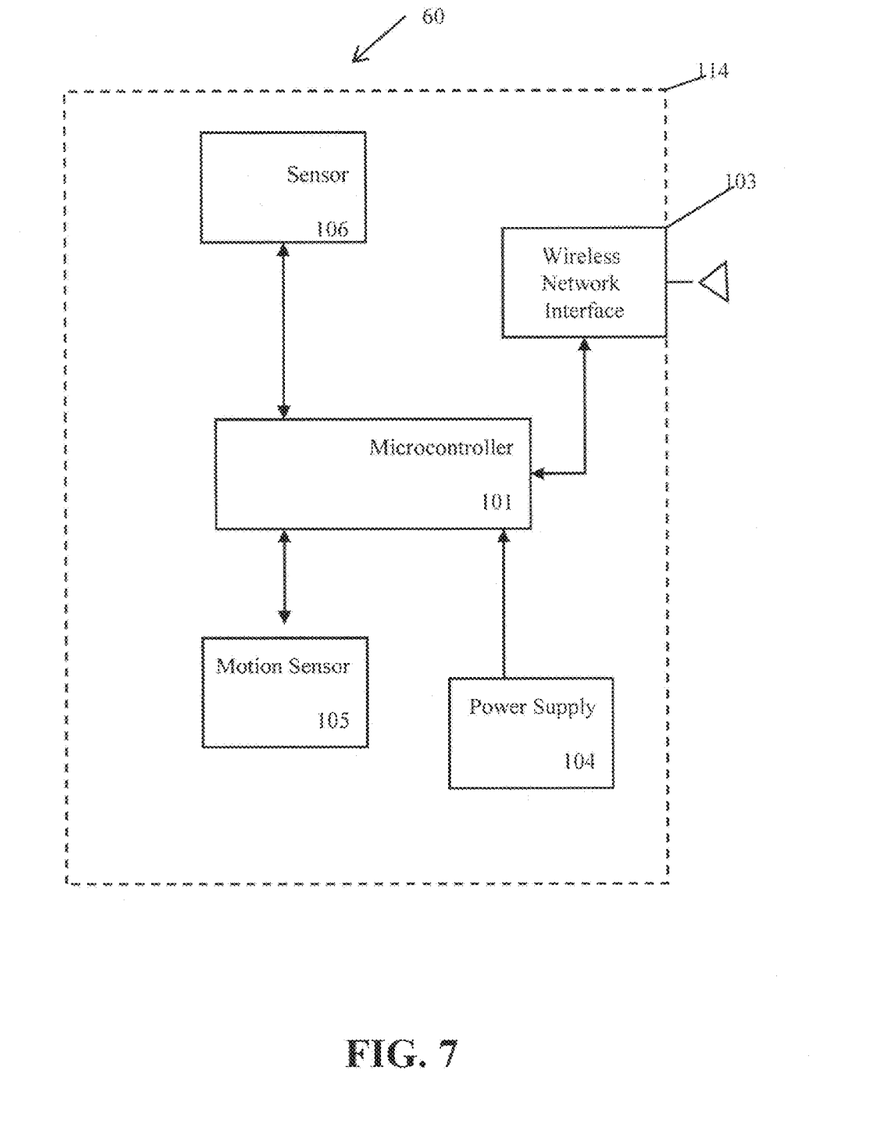
FIG. 7 is a block diagram of a tag.

A tag 60 utilized with a device 100 is illustrated in FIG. 7. The tag 60 preferably includes a microcontroller 101, a transceiver 103, a power supply 104 and a sensor 106. Alternatively, the tag 60 includes a motion sensor 105. The transmissions are transmitted through transceiver 103. A power supply 104 provides power to the tag 60. All of the components are preferably contained within a housing 107. A communication device 59 preferably has the same components and structure of the tag 60 illustrated in FIG. 7.

Figure 8:
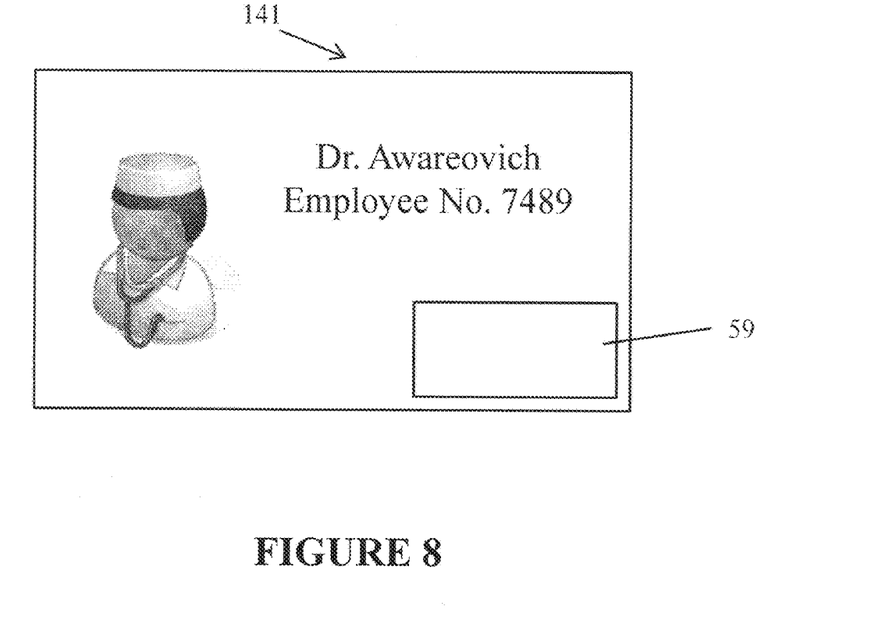
FIG. 8 is a plan view of an identification badge containing a communication device.

As shown in FIG. 8, an identification badge 141 is preferably utilized as a support for a communication device 59 for a person 58. Alternatively, the identification badge 141 is the communication device 59.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

I claim as my invention:

1. A system for determining a business relationship between individuals within a facility, the system comprising:
a plurality of first tags, each of the plurality of first tags attached to a first object, each of the plurality of first tags transmitting a wireless signal;
a plurality of second tags, each of the plurality of second tags attached to a second object, each of the plurality of second tags transmitting a wireless signal;
a mesh network comprising a plurality of plug-in sensors located within the facility and utilized for infrastructure-based real-time location tracking of objects in the facility, each plug-in sensor of the plurality of plug-in sensors communicating with other plug-in sensors of the plurality of plug-in sensors utilizing a wireless communication format, wherein each of the plurality of plug-in sensors operates in a geo-spatially fixed physical location in the facility, the mesh network receiving the wireless signal from each of the plurality of first tags and the mesh network receiving the wireless signal from each of the plurality of second tags; and
an information engine in communication with the mesh network and receiving tracking tag information for each of the plurality of first tags and each of the plurality of second tags, the information engine determining a business relationship between a first object having a first tag of the plurality of first tags and a second object having a second tag of the plurality of second tags, wherein the business relationship is based on at least two of the following plurality of interaction factors comprising a time since a last interaction, an identification of a first object, an identification of a second object, a status of a first object, a status of a second object, a position location of the interaction, and a duration of the interaction, wherein the business relationship is an interaction of a patient with a staff member, an interaction of a patient with an asset, or an interaction of a staff member with an asset, and the information engine analyzes the business relationship to determine a billing charge for services, medical services provided to a patient, or a cleaning event.

2. The system according to claim 1 wherein the first object is fixed or mobile and the second object is mobile.

3. The system according to claim 1 wherein the first object is a group of objects and the second object is a group of objects.

4. The system according to claim 1 the first object is fixed and the second object is a group of objects.

5. The system according to claim 1 wherein the first object is mobile and the second object is a group of objects.

6. The system according to claim 1 wherein the first object is a group of mobile objects and the second object is a group of mobile objects.

7. The system according to claim 1 wherein the first object is a first person and the second object is a second person and the plurality of factors further comprises a position designation of the first person and a position designation of the second person.

8. The system according to claim 1 wherein the first object is a first person and the second object is a second person and the plurality of factors further comprises a number of previous interactions between the first person and the second person within a predetermined time period.

9. The system according to claim 1 wherein each of the first plurality of tags is mounted on a corresponding identification card or is an identification card.

10. The system according to claim 1 wherein the plurality of factors further comprises a previous location of the first object, a previous location of the second object and the number of other objects located near the interaction.

11. A method for determining a business relationship between individuals within a facility, the method comprising:
transmitting a wireless signal from a first tag associated with a first person;
transmitting a wireless signal from a second tag associated with a second person;
receiving the wireless signal from the first tag and the wireless signal from the second tag at a mesh network established within the facility, the mesh network comprising a plurality of sensors located within the facility and utilized for infrastructure-based real-time location tracking of objects and individuals in the facility, each sensor of the plurality of sensors communicating with other sensors of the plurality of plug-in sensors utilizing a wireless communication format;
transmitting data from the mesh network to an information engine, the data comprising the wireless signal from the first tag and the wireless signal from the second tag;
determining at the information engine that an interaction is occurring between the first person and the second person based on the signal from the first tag and the signal from the second tag; and determining at the information engine a business relationship between the first person and the second person based on at least one of a plurality of factors comprising a position location of the interaction, a duration of the interaction, a previous location of the first person prior to the interaction, a previous location of the second person prior to the interaction and a number of other persons at the interaction, wherein the business relationship is an interaction of a patient with a staff member, an interaction of a patient with an asset, or an interaction of a staff member with an asset, and the information engine analyzes the business relationship to determine a billing charge for services, medical services provided to a patient, or a cleaning event.

12. The method according to claim 11 wherein the plurality of factors further comprises a position designation of the first person, a number of previous interactions between the first person and the second person within a predetermined time period, and a position designation of the second person.

13. A system for determining a business relationship between individuals within a facility, the system comprising:
   a plurality of peer-to-peer communication devices, each of the plurality of peer-to-peer communication devices associated with an individual person, each of the plurality of peer-to-peer communication devices transmitting a wireless signal;
   a plurality of tags, each of the plurality of tags representing a first object, each of the plurality of tags transmitting a wireless signal;
   a mesh network comprising a plurality of plug-in sensors located within the facility and utilized for infrastructure-based real-time location tracking of objects and persons in the facility, each plug-in sensor of the plurality of plug-in sensors communicating with other plug-in sensors of the plurality of plug-in sensors utilizing a wireless communication format, the mesh network receiving the wireless signal from each of the plurality of tags and the mesh network receiving the wireless signal from each of the plurality of peer-to-peer communication devices; and
   an information engine in communication with the mesh network and configured to receive data from the mesh network, the data comprising the wireless signal from each of the plurality of tags and the wireless signal from each of plurality of peer-to-peer communication devices, the information engine analyzing a business relationship between a first object and an individual person based on at least two of a plurality of factors comprising a position location of the interaction, a duration of the interaction, a previous location of the first person prior to the interaction, a time since a last interaction, identification of a first object, identification of a second object, a status of a first object, a status of a second object, and information for a mobile object within a predetermined distance of the location of the interaction, wherein the business relationship is an interaction of a patient with a staff member, an interaction of a patient with an asset, or an interaction of a staff member with an asset, and the information engine analyzes the business relationship to determine a billing charge for services, medical services provided to a patient, or a cleaning event.

14. The system according to claim 13 wherein the information engine analyzes the interaction to determine a billing charge for services of the first person.

15. The system according to claim 13 wherein the facility is a hospital and the information engine analyzes the interaction to determine medical services provided to a patient.

16. A system for analyzing an action of an individual, the system comprising:
   a plurality of tracking devices, each of the plurality of tracking devices associated with an individual person;
   a plurality of tags, each of the plurality of tags associated with a mobile object;
   a mesh network comprising a plurality of sensors positioned within a facility and utilized for infrastructure-based real-time location tracking of mobile objects and persons in the facility, each sensor of the plurality of sensors communicating with other sensors of the plurality of sensors utilizing a wireless communication format, the mesh network receiving transmissions from at least one of the plurality of tags and at least one of the plurality of tracking devices; and
   an information engine in communication with the mesh network, the information engine analyzing an action of a first person based on at least two of a plurality of factors comprising a position location of the action, a duration of the action, a previous location of the first person prior to the action, a time since a last interaction, an identification of a first object, an identification of a second object, a status of a first object, status of a second object, and information for a mobile object within a predetermined distance of the location of the action, wherein the action of the first person is an interaction of a patient with a staff member, an interaction of a patient with an asset, or an interaction of a staff member with an asset, and the information engine analyzes the action of the first person to determine a billing charge for services, medical services provided to a patient, or a cleaning event.

17. The system according to claim 16 wherein the facility is a hospital and the information engine analyzes the action to determine medical services provided to a patient.

18. The system according to claim 16 wherein the information engine analyzes the action to determine a billing charge for services of the first person.

* * * * *